(12) United States Patent
Hoard et al.

(10) Patent No.: US 12,277,740 B2
(45) Date of Patent: Apr. 15, 2025

(54) SELF-ADJUSTING BIOMETRIC SENSOR

(71) Applicant: CareFusion 303, Inc., San Diego, CA (US)

(72) Inventors: David Hoard, Escondido, CA (US); Michael Becker, San Diego, CA (US); Matias Negatu, San Diego, CA (US); Benjamin Greuel, Neenah, WI (US); Mariano Padilla, Zapopan (MX)

(73) Assignee: CareFusion 303, Inc., San Diego, CA (US)

( * ) Notice: Subject to any disclaimer, the term of this patent is extended or adjusted under 35 U.S.C. 154(b) by 434 days.

(21) Appl. No.: 17/733,490

(22) Filed: Apr. 29, 2022

(65) Prior Publication Data

US 2022/0351481 A1     Nov. 3, 2022

Related U.S. Application Data

(60) Provisional application No. 63/181,836, filed on Apr. 29, 2021.

(51) Int. Cl.
    *G06K 9/00*     (2022.01)
    *G06V 10/12*     (2022.01)
    (Continued)

(52) U.S. Cl.
    CPC .......... *G06V 10/12* (2022.01); *G06V 10/993* (2022.01); *G06V 40/00* (2022.01); *G07F 11/52* (2013.01); *G16H 20/13* (2018.01)

(58) Field of Classification Search
    CPC ........ G16H 40/60; G16H 40/63; G16H 40/67; G16H 20/10; G16H 20/13; G16H 20/00;
    (Continued)

(56) References Cited

U.S. PATENT DOCUMENTS 6,652,099 B2    11/2003   Chae et al.
7,418,115 B2    8/2008   Northcott et al.
(Continued)

FOREIGN PATENT DOCUMENTS

CN      109595441 A     4/2019
CN      208917732 U   *   5/2019
(Continued)

*Primary Examiner* — Atiba O Fitzpatrick
(74) *Attorney, Agent, or Firm* — Mintz Levin Cohn Ferris Glovsky and Popeo, P.C.

(57) ABSTRACT

A biometric sensor may include a scanner configured to capture a biometric data and an adjustment mechanism configured to respond to a force applied to the biometric sensor by shifting the biometric sensor from a neutral position to an adjusted position. The adjustment mechanism may be configured to respond to the removal of the force by returning the biometric sensor to the neutral position. While the biometric sensor is in the neutral position, the scanner may be capable of capturing a biometric data of a majority of users interacting with the apparatus. Accordingly, the biometric sensor may be able to operate with minimal adjustments. The biometric sensor may be part of a dispensing cabinet such that the biometric data captured by the biometric sensor may be used to control access to the dispensing cabinet. Related methods are also disclosed.

21 Claims, 9 Drawing Sheets

(51) Int. Cl.
*G06V 10/98* (2022.01)
*G06V 40/00* (2022.01)
*G07F 11/52* (2006.01)
*G16H 20/13* (2018.01)

(58) Field of Classification Search
CPC ........ G16H 70/40; G16H 40/00; G16H 40/20; G16H 70/00; G07F 17/0092; A61J 1/00; A61J 1/03; A61J 7/0076; A61J 7/0084; A61J 7/0092; A61J 7/02; A61J 7/04; A61J 7/0454; A61J 7/0427; A61J 7/0436; A61J 7/0445; A61J 7/0463; G06V 40/40; G06V 40/45; G06V 40/10; G06V 40/00; G06V 40/14; G06V 40/16; G06V 40/18; G06V 40/193; G06V 40/197; G06V 40/20; G06V 40/23; G06V 40/25; G06V 40/60; G06V 40/63; G06V 40/67; G06V 40/70; G06V 40/107; G06V 40/11; G06V 40/113; G06V 40/117; G06V 40/12; G06V 40/1306; G06V 40/1312; G06V 40/168; G06V 40/173; G06V 40/172; G06V 40/19; G06F 21/32
See application file for complete search history.

(56) References Cited

U.S. PATENT DOCUMENTS

| | | | |
|---|---|---|---|
| 7,428,320 B2 | 9/2008 | Northcott et al. | |
| 7,605,709 B2 | 10/2009 | Tolliver | |
| 7,665,914 B2 | 2/2010 | Chang | |
| 7,869,627 B2 | 1/2011 | Northcott et al. | |
| 8,014,571 B2 | 9/2011 | Friedman et al. | |
| 8,132,912 B1 | 3/2012 | Northcott et al. | |
| 8,317,325 B2 | 11/2012 | Raguin et al. | |
| 8,317,609 B2 | 11/2012 | Morrow | |
| 9,195,890 B2 | 11/2015 | Bergen | |
| 9,256,719 B2 * | 2/2016 | Berini | G06V 40/197 |
| 9,256,720 B2 | 2/2016 | Berini et al. | |
| 9,336,438 B2 | 5/2016 | Malhas et al. | |
| 10,054,802 B2 | 8/2018 | Bishop et al. | |
| 10,068,078 B2 | 9/2018 | Dass | |
| 10,503,974 B2 | 12/2019 | Su et al. | |
| 10,517,520 B2 | 12/2019 | Bott et al. | |
| 10,592,740 B2 | 3/2020 | Abe et al. | |
| 10,628,692 B2 | 4/2020 | Olie et al. | |
| 2003/0225596 A1 * | 12/2003 | Richardson | G07C 9/257 705/2 |
| 2008/0117298 A1 | 5/2008 | Torres | |
| 2009/0041309 A1 * | 2/2009 | Kim | G06V 40/19 382/117 |
| 2012/0323362 A1 * | 12/2012 | Paydar | G07F 9/002 29/434 |
| 2013/0215275 A1 * | 8/2013 | Berini | G06V 10/993 348/150 |
| 2014/0288698 A1 * | 9/2014 | Handfield | G07F 11/24 700/231 |
| 2019/0050626 A1 * | 2/2019 | Berini | G06F 21/34 |
| 2022/0351121 A1 * | 11/2022 | Dattamajumdar | G16H 40/20 |

FOREIGN PATENT DOCUMENTS

| | | |
|---|---|---|
| CN | 210295134 U | 4/2020 |
| CN | 211951984 U | 11/2020 |
| CN | 212361403 U | 1/2021 |
| KR | 2003-0019227 A | 3/2003 |

* cited by examiner

SELF-ADJUSTING BIOMETRIC SENSOR

CROSS REFERENCE TO RELATED APPLICATION

This application claims priority to U.S. Provisional Application No. 63/181,836, entitled "SELF-ADJUSTING BIOMETRIC SENSOR" and filed on Apr. 29, 2021, the disclosure of which is incorporated herein by reference in its entirety.

TECHNICAL FIELD

The subject matter described herein relates generally to biometric authentication and more specifically to a self-adjusting biometric sensor.

BACKGROUND

Diversion may refer to the transfer of a controlled and/or high-value substance to a third party who is not legally authorized to receive, possess, and/or consume the substance for personal use or personal gain. High-value and/or controlled prescription medications, notably opioids, may be especially prone to diversion. For instance, a prescription pain medication may be diverted when a user keeps the prescription pain medication for unauthorized personal use instead of administering the prescription pain medication to a patient or wasting the prescription pain medication. As such, diversion detection, investigation, and prevention may require surveillance of various interactions with high-value and/or controlled substances.

SUMMARY

Systems, methods, and articles of manufacture are provided for a self-adjusting biometric sensors configured to capture one or more biometric identifiers including, for example, fingerprint, palm veins, facial geometry, palm print, hand geometry, iris pattern, retina pattern, voice, typing rhythm, gait, signature, and/or the like. The self-adjusting biometric sensor may be configured to automatically return to a neutral position (or resting position) after being shifted out of the neutral position. In the neutral position, the self-adjusting biometric sensor may have a capture region that is suitable for capturing the biometric data associated with a threshold quantity of users. For example, while the self-adjusting biometric sensor is in the neutral position, the eyes of a threshold quantity of users may be within the field of view and/or angle of view of the self-adjusting biometric sensor. As such, the self-adjusting biometric sensor may be capable of capturing the biometric data of a majority of users without any adjustments. For a user who requires adjustments, for example, to raise or lower the field of view and/or angle of view, the self-adjusting biometric sensor may return to the neutral position after the self-adjusting biometric sensor has captured the user's biometric data. Accordingly, although the self-adjusting biometric sensor is capable of adapting to different users, the self-adjusting biometric sensor may nevertheless operate with minimal adjustments.

In one aspect, there is provided a dispensing cabinet with a biometric sensor that is configured to return to a neutral position. The biometric sensor may include: a scanner configured to capture a biometric data, and an adjustment mechanism configured to respond to a force applied to the biometric sensor by shifting the biometric sensor from a neutral position to an adjusted position, the adjustment mechanism further being configured to respond to the removal of the force by returning the biometric sensor to the neutral position, the scanner being able to capture a first biometric data of a first user while the biometric sensor is in the neutral position, and the scanner being able to capture a second biometric data of a second user while the biometric sensor is in the adjusted position. The dispensing cabinet may further include: a storage container; a fastener configured to secure one or more contents of the storage container; and a controller having at least one data processor configured to receive, from the biometric sensor, the first biometric data and/or the second biometric data, and control, based at least on the first biometric data and/or the second biometric data, the fastener securing the one or more contents of the storage container.

In some variations, one or more features disclosed herein including the following features can optionally be included in any feasible combination. The biometric sensor in the neutral position may be able to capture the biometric data of a threshold quantity of users interacting with the dispensing cabinet including the first user.

In some variations, the neutral position of the biometric sensor may be determined based at least on a height and/or an angle at which the biometric sensor is mounted on the dispensing cabinet.

In some variations, the neutral position of the biometric sensor may be determined based at least on one or more physical characteristics of users interacting with the dispensing cabinet.

In some variations, the one or more physical characteristics may include a height distribution of the users interacting with the dispensing cabinet.

In some variations, the neutral position of the biometric sensor may be determined based at least on a frequency and/or a magnitude of adjustments made to the biometric sensor.

In some variations, the adjustment mechanism may include a first assembly disposed on one end of the biometric sensor and a second assembly disposed on an opposite end of the biometric sensor. The first assembly may include a first pivot hinge coupled with a first spring, a first bearing, and a first bearing holder. The second assembly may include a second pivot hinge coupled with a second spring, a second bearing, and a second bearing holder.

In some variations, the first spring and the second spring may be configured to respond to the force by shifting the biometric sensor from the neutral position to the adjusted position. The first spring and the second spring may be further configured to provide an opposite force for returning the biometric sensor to the neutral position.

In some variations, the scanner may be disposed on a printed circuit board assembly (PCBA) that is mechanically and electrically coupled to a cable. The cable may be threaded through an aperture in the first assembly or the second assembly.

In some variations, the cable may be configured to convey a signal between the scanner and the controller.

In some variations, the biometric sensor may further include a housing and a main body assembly configured to form a cavity when coupled with the housing. The printed circuit board assembly including the scanner may be disposed at least partially inside the cavity.

In some variations, the biometric sensor may further include a front cover coupled with the main body assembly.

The biometric sensor may be configured to protect a lens assembly of the scanner included in the printed circuit board assembly.

In some variations, the adjustment mechanism may include one or more features configured to prevent the biometric sensor from being shifted more than a threshold quantity beyond the neutral position.

In some variations, the one or more features may include a ridge and/or a protrusion in a housing of the biometric sensor that interacts with a spring and/or a bearing holder to prevent the biometric sensor from being shifted more than the threshold quantity beyond the neutral position.

In some variations, the one or more features may include a ridge and/or a protrusion in a bearing holder that interacts with a spring to prevent the biometric sensor from being shifted more than the threshold quantity beyond the neutral position.

In some variations, the one or more features may include a hinge having a rotational limit.

In some variations, the biometric data may include palm veins, a facial geometry, a palm print, a hand geometry, an iris pattern, a retina pattern, a voice, a typing rhythm, a gait, and/or a signature.

In some variations, the adjustment mechanism may include a motor. The controller may be further configured to: determine a quality level of the first biometric data; determine the quality level is below a threshold quality level; and activate the motor to adjust the neutral position of the biometric scanner in order to increase the quality level of the second biometric data.

In some variations, the controller may be further configured to: detect the biometric sensor being shifted from the neutral position to the adjusted position; in response to detecting the biometric sensor being shifted from the neutral position to the adjusted position, record a magnitude of the shift and update a quantity of adjustments made to the biometric scanner; and in response to the quantity of adjustments exceeding a threshold value, provide an output indicating a recommended configuration for the biometric sensor, the recommended configuration corresponding to the magnitude of the shift recorded over a period of time.

In another aspect, there is provide a method that includes: capturing, by a scanner of a biometric sensor in a neutral position, a first biometric data of a first user, the biometric sensor having an adjustment mechanism configured to respond to a force applied to the biometric sensor by shifting the biometric sensor from the neutral position to an adjusted position, the adjustment mechanism further being configured to respond to the removal of the force by returning the biometric sensor to the neutral position, the scanner being able to capture the first biometric data of the first user while the biometric sensor is in the neutral position, and the scanner being able to capture a second biometric data of a second user while the biometric sensor is in the adjusted position; capturing, by the scanner of the biometric sensor in the adjusted position, the second biometric data of the second user; receiving, at a controller having at least one data processor, the first biometric data and/or the second biometric data from the biometric sensor; and controlling, by the controller and based at least on the first biometric data and/or the second biometric data, a fastener securing one or more contents of a storage container of a dispensing cabinet.

The details of one or more variations of the subject matter described herein are set forth in the accompanying drawings and the description below. Other features and advantages of the subject matter described herein will be apparent from the description and drawings, and from the claims. While certain features of the currently disclosed subject matter are described for illustrative purposes in relation to biometric-based diversion detection, investigation, and prevention, it should be readily understood that such features are not intended to be limiting. The claims that follow this disclosure are intended to define the scope of the protected subject matter.

DESCRIPTION OF DRAWINGS

The accompanying drawings, which are incorporated in and constitute a part of this specification, show certain aspects of the subject matter disclosed herein and, together with the description, help explain some of the principles associated with the disclosed implementations. In the drawings.

When practical, similar reference numbers denote similar structures, features, or elements.

DETAILED DESCRIPTION

Diversion of a medication may occur at any point in time during the lifecycle of the medication including, for example, the shipping, receiving, stocking, dispensing, administration, and/or wasting of the medication. Prescription pain medications may be especially prone to diversion due to a lack of sufficient custodial oversight during, for instance, the shipping, receiving, stocking, dispensing, administration, and/or wasting of the prescription pain medication. The detection, investigation, and prevention of diversion may therefore require surveillance during each stage of the lifecycle of the prescription pain medication in order to identify the different individuals who interact with the prescription pain medication during the shipping, receiving, stocking, dispensing, administration, and/or wasting of the prescription pain medication. To that end, biometric sensors may provide a robust and efficient mechanism for identifying and authenticating these individuals. However, conventional biometric sensors may be difficult to integrate into existing medication management systems and established clinical workflows.

In some example embodiments, a self-adjusting biometric sensor may be configured to capture one or more biometric identifiers including, for example, fingerprint, palm veins, facial geometry, palm print, hand geometry, iris pattern, retina pattern, voice, typing rhythm, gait, signature, and/or the like. The self-adjusting biometric sensor may be configured to operate with minimal adjustments by at least automatically returning to a neutral position in which the self-adjusting biometric sensor is capable of capturing the biometric data associated with a threshold quantity of users. For example, while the self-adjusting biometric sensor is in the neutral position, the eyes of a threshold quantity of users may be within the field of view and/or angle of view of the self-adjusting biometric sensor. As such, the self-adjusting biometric sensor may be capable of capturing the biometric data of a majority of users without any adjustments. Minimizing the need to adjustments may minimize opportunities of user error and prevent unnecessary wear on the self-adjusting biometric sensor. For other users, the field of view and/or angle of view of the self-adjusting biometric sensor may be adjusted (e.g., raised, lowered, tilted, rotated, and/or the like) to capture the biometric data of these users before returning to the neutral position. In doing so, the self-adjusting biometric sensor may remain capable of adapting to different users.

Figure 1:
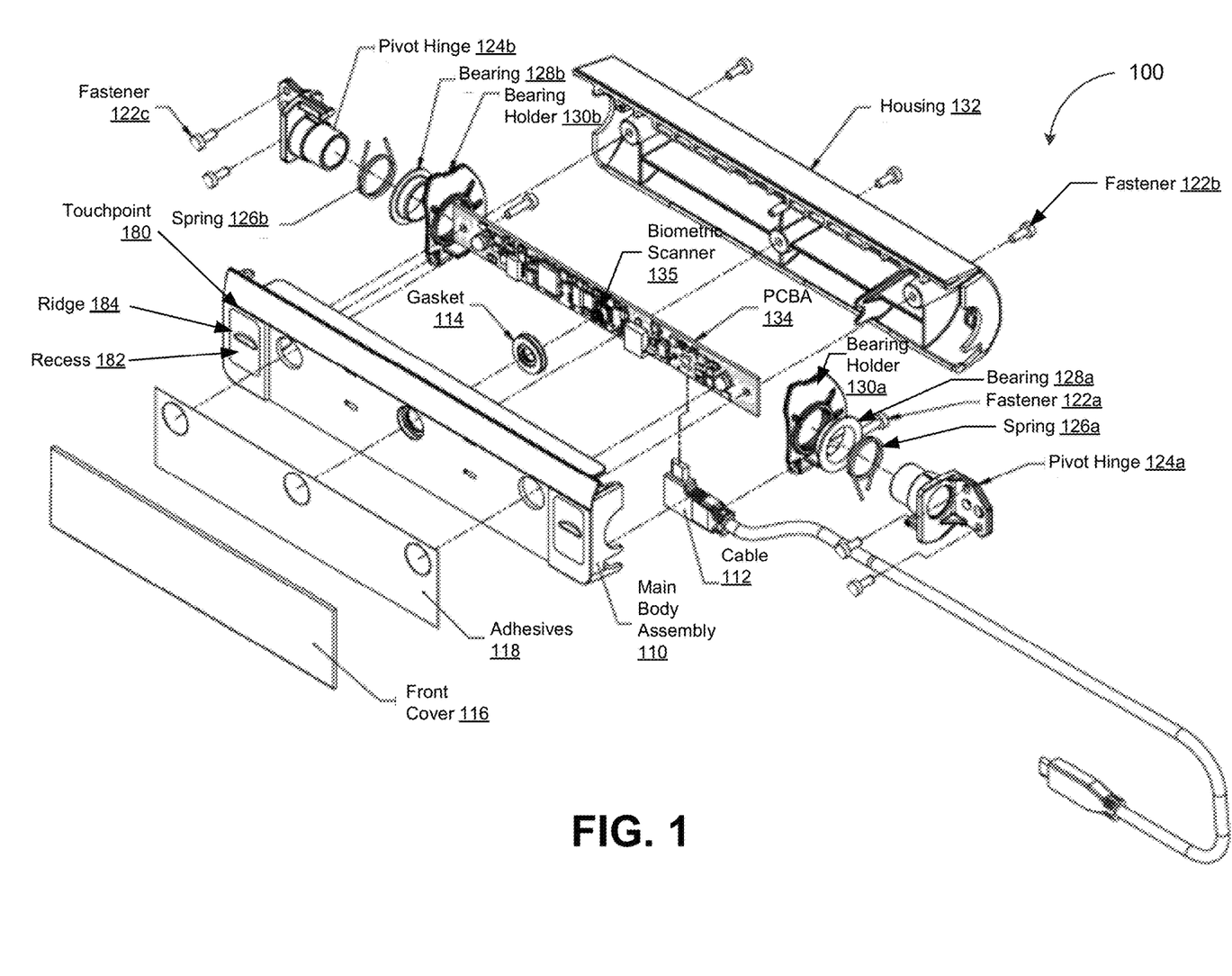
FIG. 1 depicts an exploded view of an example of a biometric sensor, in accordance with some example embodiments.
Figure 2:
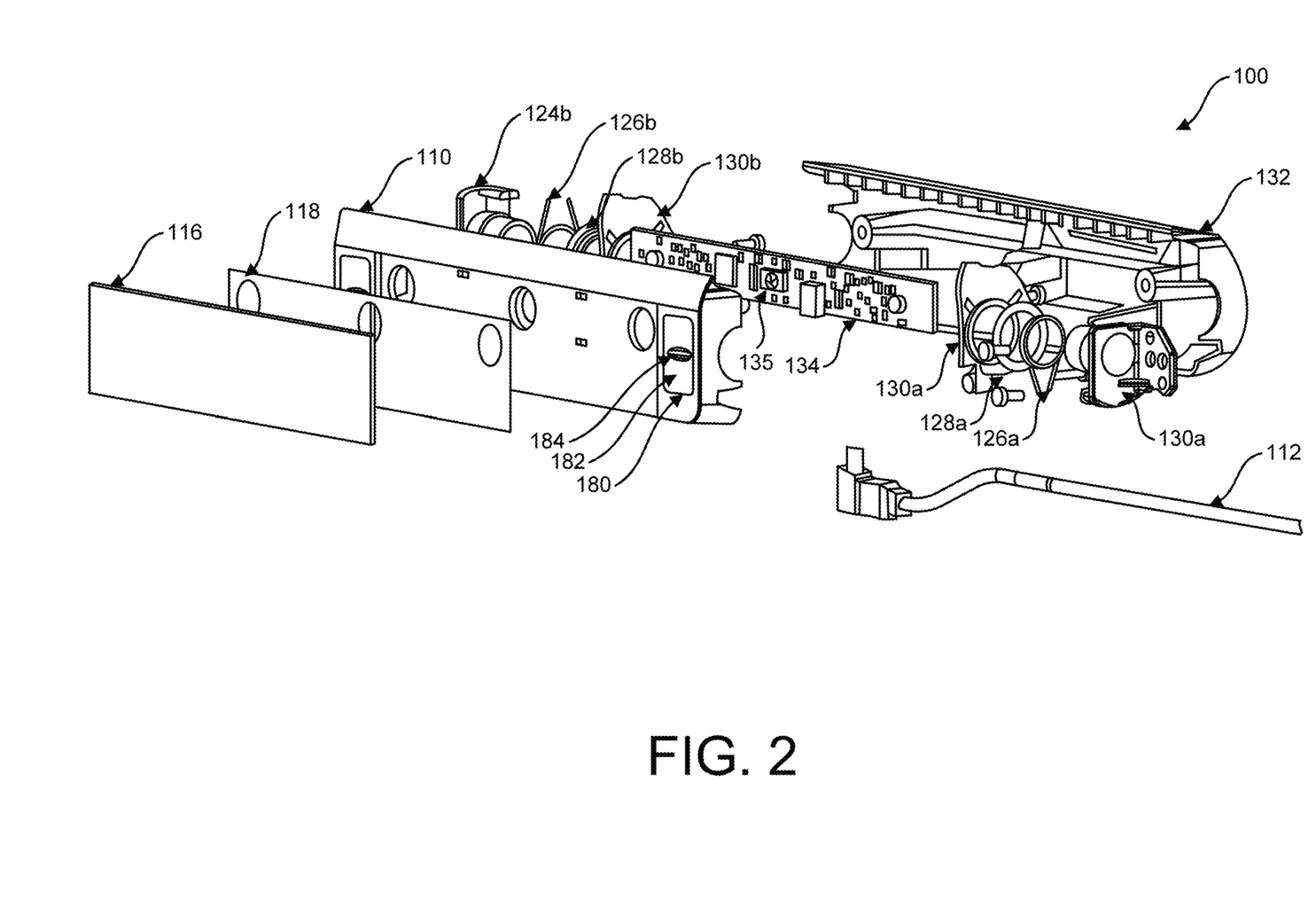
FIG. 2 depicts another exploded view of an example of a biometric sensor, in accordance with some example embodiments.
Figure 3:
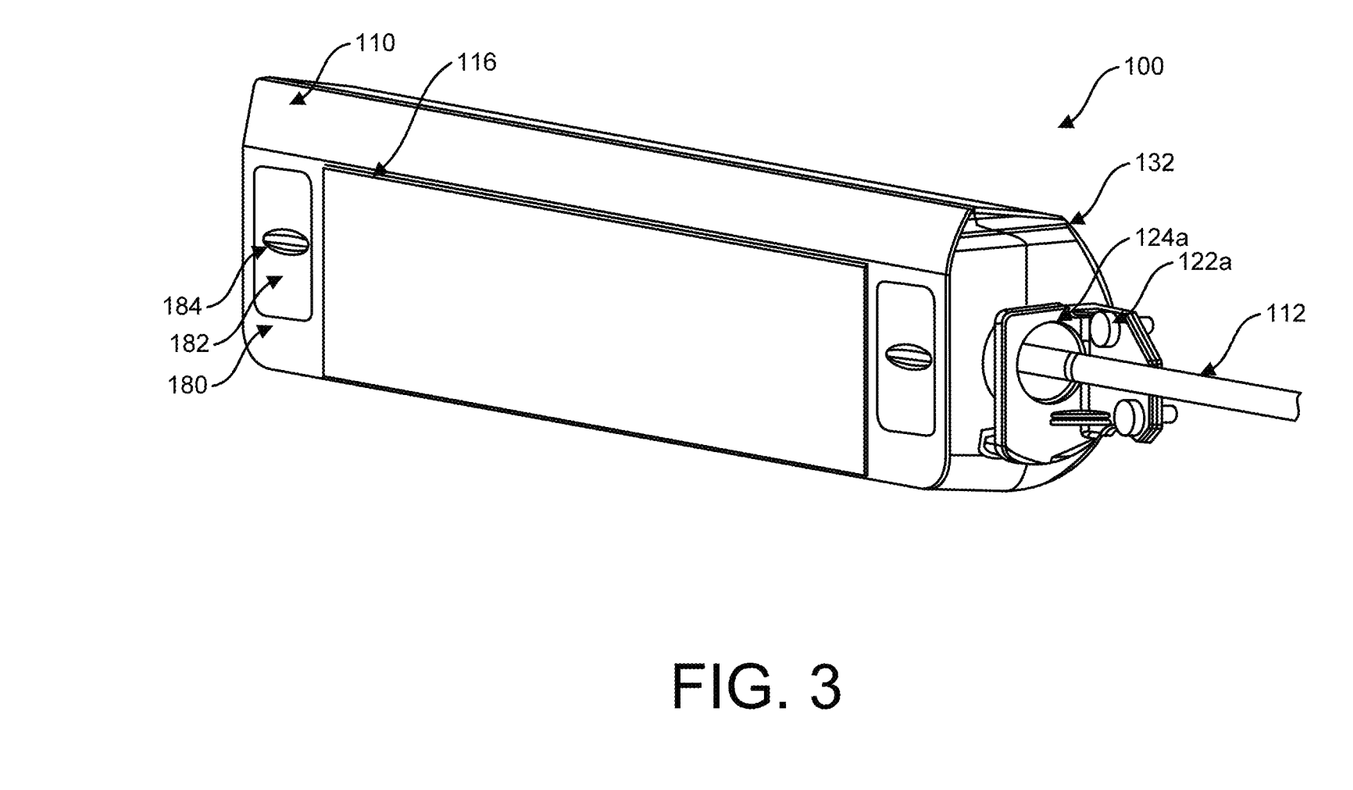
FIG. 3 depicts an assembled view of an example of a biometric sensor, in accordance with some example embodiments.
Figure 4:
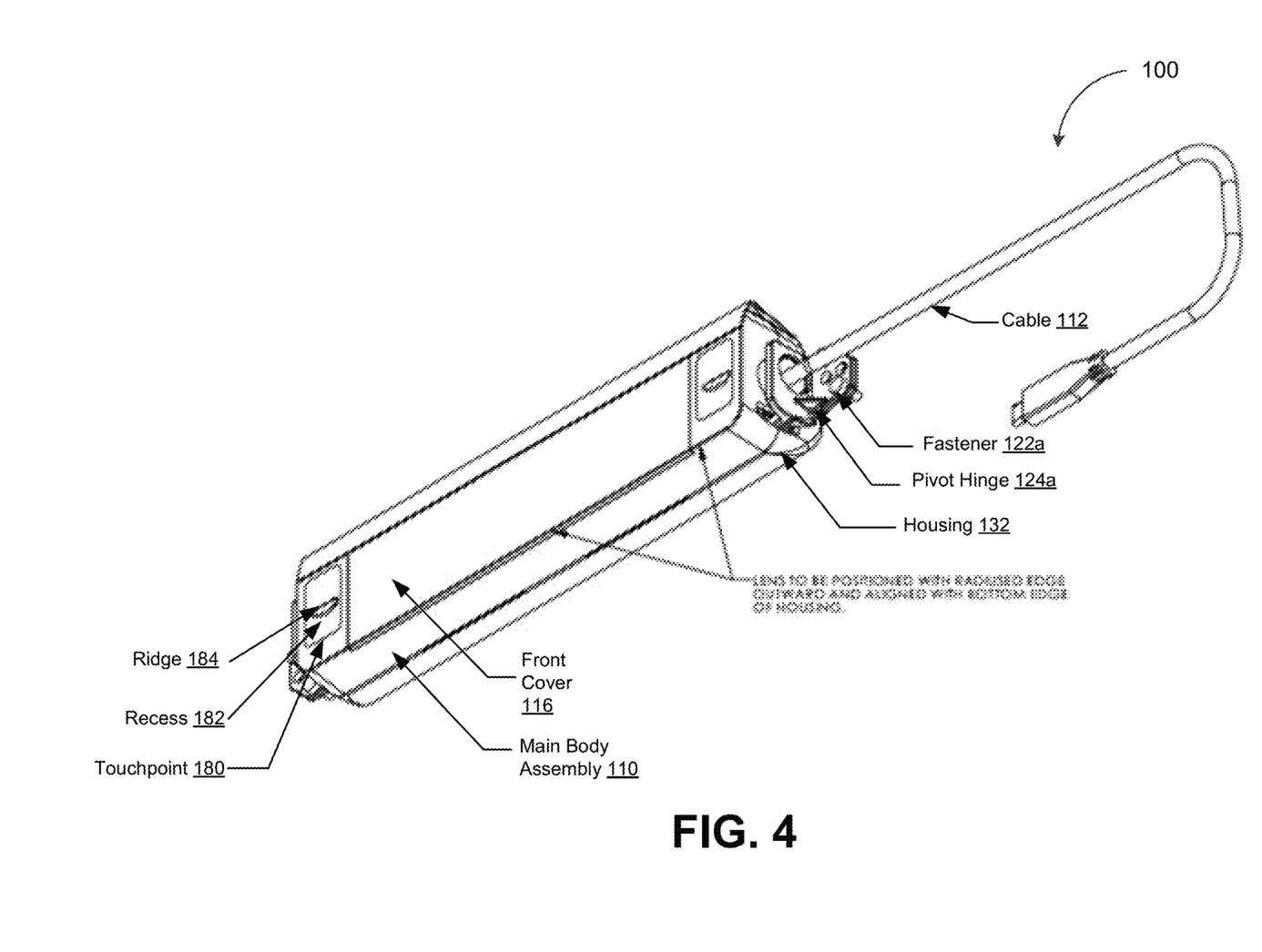
FIG. 4 depicts another assembled view of an example of a biometric sensor, in accordance with some example embodiments.
Figure 5:
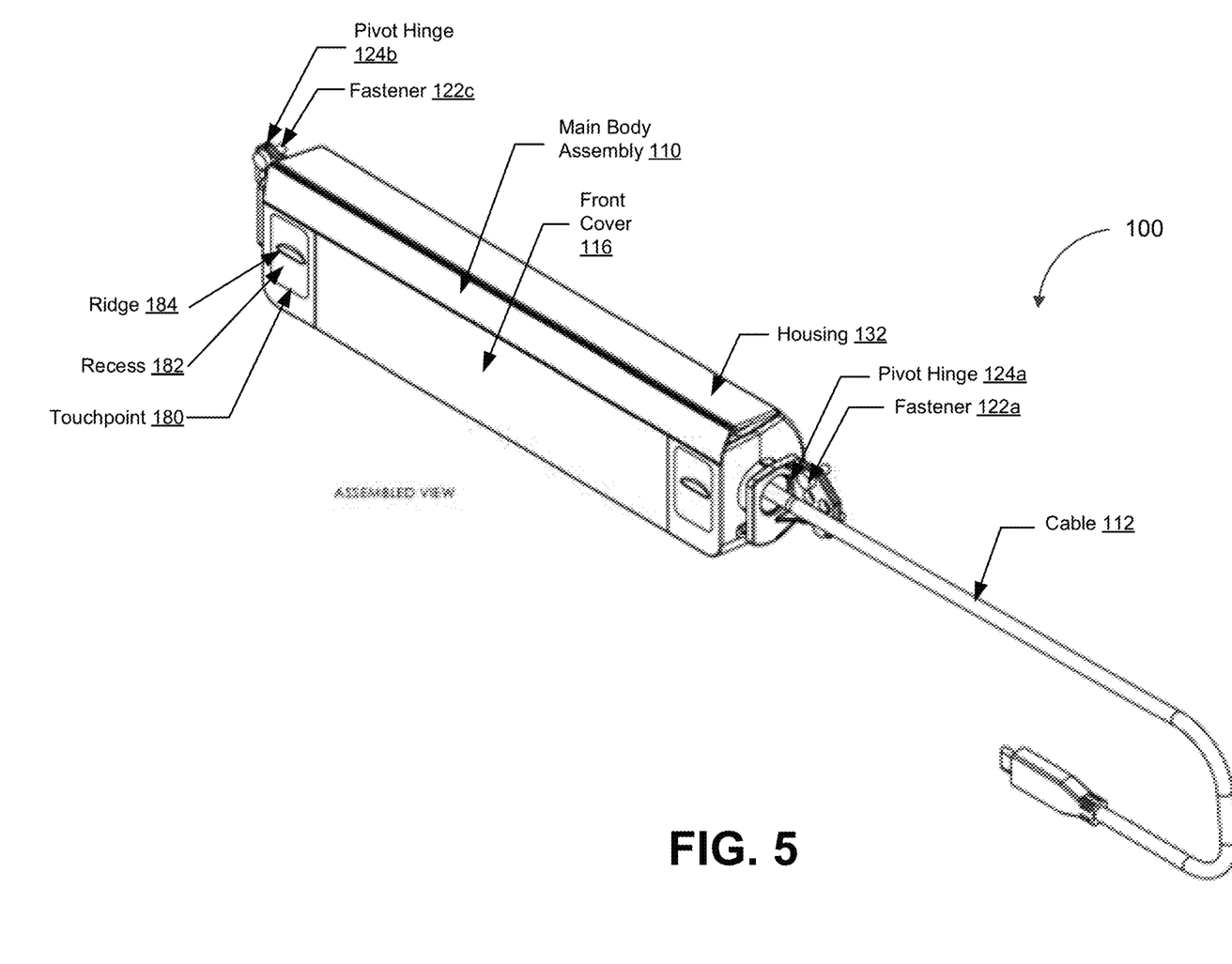
FIG. 5 depicts another assembled view of an example of a biometric sensor, in accordance with some example embodiments.
Figure 6:
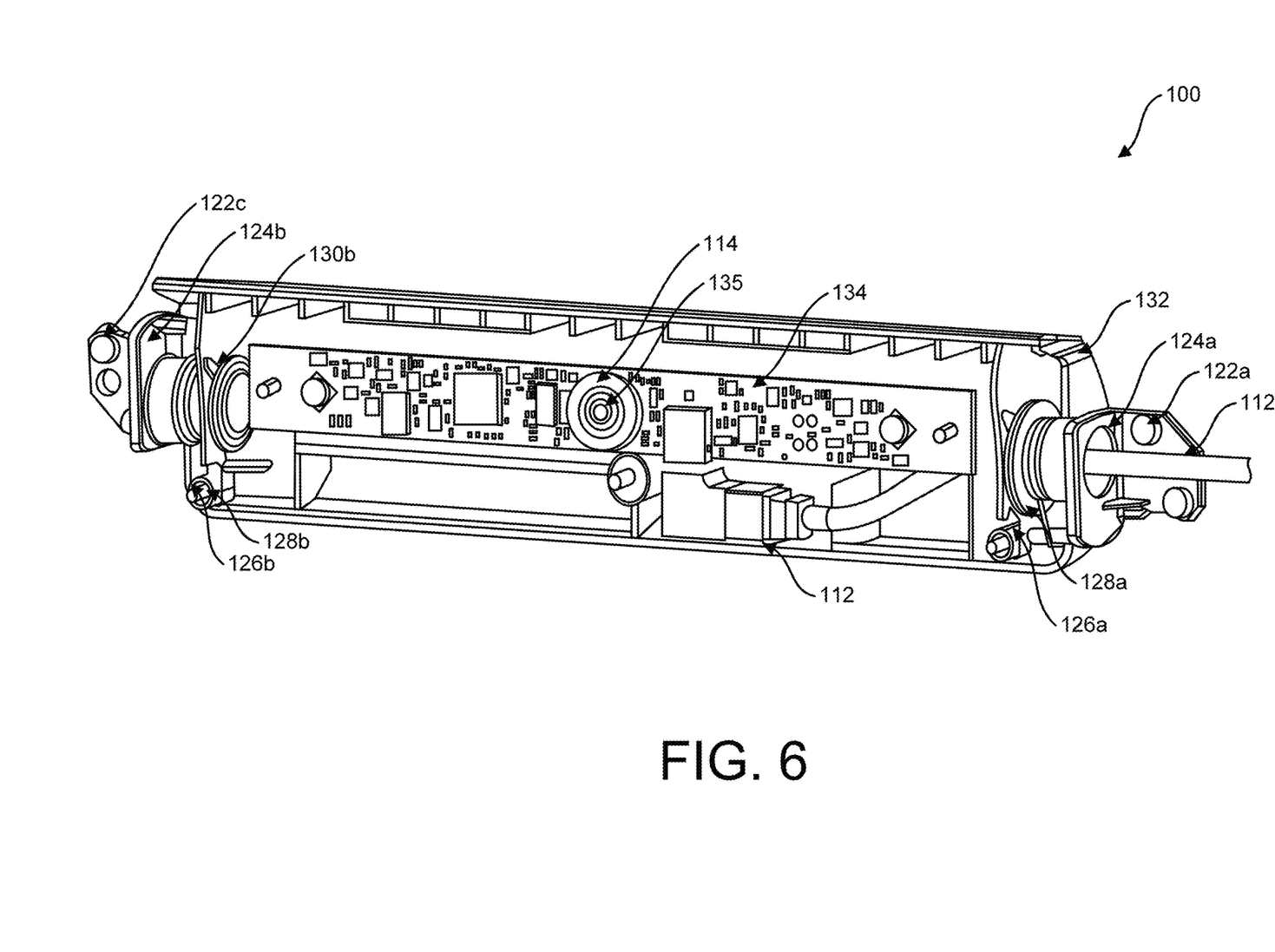
FIG. 6 depicts an interior view of an example of an assembled biometric sensor, in accordance with some example embodiments.
Figure 7:
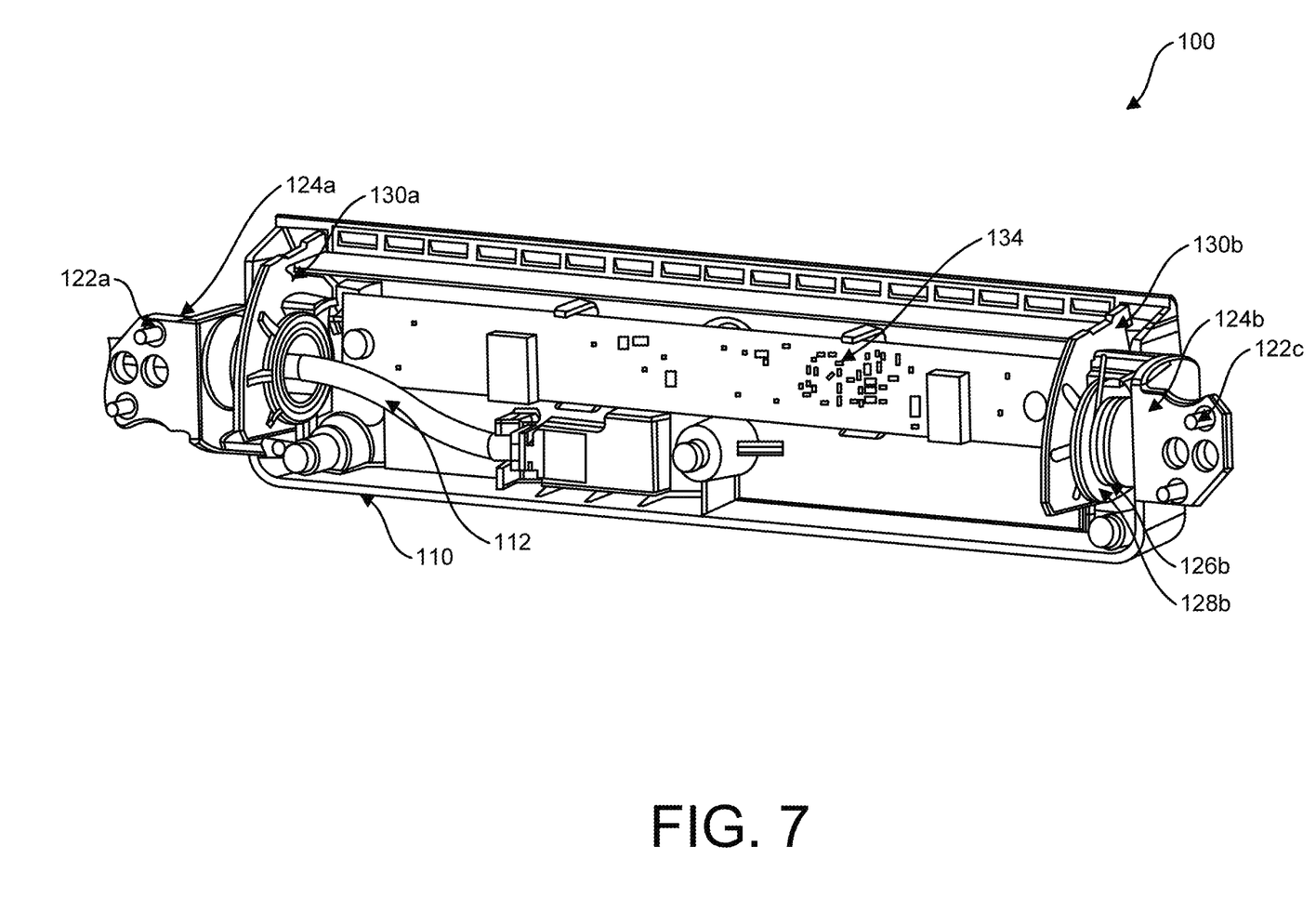
FIG. 7 depicts another interior view of an example of an assembled biometric sensor, in accordance with some example embodiments.

FIGS. 1-2 depict exploded views of an example of a biometric sensor 100, in accordance with some example embodiments. Assembled views of the biometric sensor 100 are shown in FIGS. 3-5 while FIGS. 6-7 depict interior views of the biometric sensor 100. Referring to FIGS. 1-2, the biometric sensor 100 may include a main body assembly 110, a cable 112, a gasket 114, a front cover 116, adhesives 118, fasteners 122, pivot hinges 124, springs 126, bearings 128, bearing holders 130, a housing 132, and a printed circuit board assembly (PCBA) 134. In some example embodiments, the printed circuit board assembly 134 may include a biometric scanner 135 configured to capture one or more biometric identifiers including, for example, fingerprint, palm veins, facial geometry, palm print, hand geometry, iris pattern, retina pattern, voice, typing rhythm, gait, signature, and/or the like. In some embodiments, the biometric scanner 135 may be dynamically activated such as in response to an input value indicating consent to biometric data collection for a user. For example, the user may present a badge or other credentials to access the system. Once authorized, the system may receive consent from the user (e.g., via a graphical user interface) to collect biometric data from the user for future access attempts.

As shown in FIGS. 1-7, the printed circuit board assembly 134, including the biometric scanner 135, may be enclosed within a cavity formed by the main body assembly 110 and the housing 132. The printed circuit board assembly 134 may be mechanically and electrically coupled to the cable 112, which may convey signals from the biometric scanner 135 to a controller (e.g., an AD board and/or the like) configured to further process the biometric data (e.g., iris patterns and/or the like) captured by the biometric scanner 135.

In the example shown in FIGS. 1-7, the printed circuit board assembly 134 may be secured to the main body assembly 110 and/or the housing 132 using one or more fasteners such as a first fastener 122*a*, a second fastener 122*b*, and/or the like. In some cases, the lenses of the biometric sensor 135 may be positioned with its radiused edge (e.g., rounded or curved edge) facing outward and aligned with, for example, the bottom edge of the housing 132. The gasket 114, which may be configured to seal and protect, for example, the lenses included in the biometric scanner 135, may be interposed between the biometric scanner 135 on the printed circuit board 134 and the main body assembly 110. Furthermore, in the example shown in FIGS. 1-7, the main body assembly 110 may be secured to the housing 132 using one or more fasteners such the first fastener 122*a*, the second fastener 122*b*, and/or the like. However, it should be appreciated that the printed circuit board assembly 134, the main body assembly 110, and the housing 132 may be secured using any retention mechanism including, for example, snap-fit, friction-fit, magnets, adhesives, and/or the like.

Referring again to FIGS. 1-2, the main body assembly 110 may be further coupled to the front cover 116 by the adhesives 118. The front cover 116 may provide additional protection for the biometric scanner 135 (e.g., the lens assembly of the biometric scanner 135) included in the printed circuit board 134. An additional protective film may be disposed on a front surface of the front cover 116 and may be kept on the front surface of the front cover 116 during manufacturing, assembly, and shipping of the biometric sensor 100.

In some example embodiments, the biometric sensor 100 may be configured with a neutral position (or resting position) at which the biometric scanner 135 is able to capture the biometric data associated with a threshold quantity of users. For example, while the biometric sensor 100 is in the neutral position, the eyes of a threshold quantity of users may be within the field of view and/or angle of view of the biometric scanner 135. The neutral position of the biometric sensor 100 may be defined by one or more metrics including, for example, a height, an angle of rotation, and/or the like. Moreover, the neutral position of the biometric sensor 100 may be determined based on the height and/or angle at which the biometric sensor 100 is mounted. Alternatively and/or additionally, the neutral position of the biometric sensor 100 may be determined based on the physical characteristics of the users interacting with the biometric sensor 100. For instance, the neutral position of the biometric sensor 100 may be determined based on a height distribution (e.g., mean, median, mode, range, and/or the like) of the users expected to interact with the biometric sensor 100.

The neutral position of the biometric sensor 100 may be fixed during manufacturing and be subject to subsequent reconfiguration. In particular, if more than a threshold quantity of adjustments are detected at the biometric sensor 100 subsequent to deployment, the neutral position of the biometric sensor 100 may be reconfigured accordingly. For example, if the biometric sensor 100 is raised (or lowered) from the neutral position at an above threshold frequency, the neutral position of the biometric sensor 100 may be raised (or lowered) in order to minimize the need to adjust the biometric sensor 100.

Alternatively and/or additionally, the neutral position of the biometric sensor 100 may be reconfigured if the biometric sensor 100 is rotated upwards (or downwards) from the neutral position at an above threshold frequency. The magnitude of these reconfigurations may correspond to the magnitude of the adjustments actually encountered at the biometric sensor 100. For example, a controller coupled with the biometric sensor 100 may detect adjustments to the position of the biometric sensor 100 and record the frequency and magnitude of these adjustments. When the frequency of the adjustments exceeds a threshold, the controller may generate an output including a recommended configuration for the biometric sensor 100. For instance, the output may indicate that the neutral position of the biometric sensor 100 should be reconfigured as well as indicate a magnitude of the adjustment, which may correspond to the distribution (e.g., mean, medium, mode, range, and/or the like) of actual adjustments encountered at the biometric sensor 100 over a period of time. Thus, the neutral position of the biometric sensor 100 may be adapted based on actual usage data in order to accommodate for the actual physical characteristics of the users interacting with the biometric sensor 100. Doing so may, as noted, minimize subsequent adjustments to the biometric sensor 100.

In some example embodiments, the biometric sensor 100 may include one or more motors (or other actuators) to automatically adjust the neutral position of the biometric sensor 100 such that the eyes of one or more users are within the field of view and/or angle of view of the biometric sensor 100. For example, a controller coupled with the biometric sensor may determine, based at least on a quality of the biometric data captured by the biometric sensor 100, whether to adjust the neutral position of the biometric sensor 100. If the quality of more than a threshold quantity (or proportion) of the biometric data captured by the biometric sensor 100 fails to meet a threshold level, the controller may activate the motor (or other actuator) to adjust the neutral position of the biometric sensor 100. In this context, the quality of the biometric data may correspond to whether the biometric data captured at the biometric sensor 100 enables an identification of the users interacting with the biometric sensor 100. Biometric data that fails to meet the quality threshold may be incomplete and/or lack sufficient clarity. Thus, an iris scan captured by the biometric sensor 100, for example, may fail to meet the quality threshold if the iris scan does not enable the identification a corresponding user.

In some example embodiments, the biometric sensor 100 may be configured to self-adjust to return to the neutral position after being shifted out of the neutral position. For instance, for users whose eyes are not in the field of view and/or angle of view of the biometric scanner 135 when the biometric scanner 135 is in the neutral position, the biometric sensor 100 may raised, lowered, tilted, and/or rotated in order to adjust the field of view and/or the angle of view of the biometric scanner 135. The biometric sensor 100 may be adjusted by applying, to the biometric sensor 100, pressure to raise, lower, and/or rotate the biometric sensor 100. That is, the biometric sensor 100 may be adjusted by one or more rectilinear shifts along an x-axis, y-axis, and/or z-axis. Alternatively and/or additionally, the adjustment to the position of the biometric sensor 100 may include rotation around a fixed axis. Once the pressure on the biometric sensor 110 is released, for example, after the biometric scanner 135 has captured the biometric data of such users, the biometric sensor 100 may automatically return to the neutral position. Because the biometric sensor 100 in the neutral position is configured to capture the biometric data associated with a majority of users, the biometric sensor 100 may operate with minimal adjustments. Nevertheless, even when adjustments are necessary, the biometric sensor 100 may return to the neutral position without intervention.

A stable and secure touchpoint for adjusting the biometric scanner 100 may be included. For example, the main body assembly 110 may include at least one touchpoint 180. The touchpoint 180 may include a recess 182 forming a depression within a face of the main body assembly 110. The recess 182 may be formed to receive a finger or structure for adjusting the biometric scanner 100. To direct an adjustment force from the finger or other adjustment structure, some touchpoints may include a ridge 184 within the recess 182. The ridge 184 may provide a purchase for the finger or other adjustment structure to prevent slipping during adjustment. The ridge 184 may also direct the adjustment pressure. For example, the touchpoint 180 can guide the adjustment force along the adjustment axis and away from a direction that might disrupt or break the biometric scanner 100. The example biometric scanner shown in FIGS. 1-5 includes two touchpoints on the front face of the main body assembly 110. The touchpoint 180 may additionally or alternatively be included on a top surface of the scanner, at the middle of the front face of the main body assembly 110, or other position that can receive an adjustment pressure without obscuring the scanner (e.g., biometric scanner 135).

In some example embodiments, the biometric sensor 100 may include a self-adjusting mechanism configured to return the biometric sensor 100 to the neutral position. As shown in FIGS. 1-2 and 6-7, the self-adjusting mechanism may include, on one end of the biometric sensor 100, a first pivot hinge 124a that is coupled with a first spring 126a, a first bearing 128a, and a first bearing holder 130a. The self-adjusting mechanism may further include, on an opposite end of the biometric sensor 100, a second pivot hinge 124b that is coupled with a second spring 126b, a second bearing 128b, and a second bearing holder 130b. To reduce cost as well as manufacturing complexity, the first pivot hinge 124a and the second pivot hinge 124b may be implemented as identical components and not complementary components.

In some example embodiments, the self-adjusting mechanism may be configured to accommodate the cable 112. For instance, as shown in FIGS. 3-7, the cable 112 may be threaded through an aperture that runs through an assembly including the first pivot hinge 124a coupled with the first spring 126a, the first bearing 128a, and the first bearing holder 130a. Moreover, as shown in FIGS. 1-7, the biometric sensor 100 may be mounted via the first pivot hinge 124a and/or the second pivot hinge 124b. For example, the first pivot hinge 124a and/or the second pivot hinge 124b may include one or more apertures for receiving one or more fasteners, such as the first fastener 122a and/or a third fastener 122c, for mounting the biometric sensor 100. However, it should be appreciated that the biometric sensor 100 may be mounted using any retention mechanism including, for example, snap-fit, friction-fit, magnets, adhesives, and/or the like.

In some example embodiments, while force may be applied against the first spring 126a and the second spring 126b to shift the biometric sensor 100 out of the neutral position, the first spring 126a and the second spring 126b may provide an opposite force to return the biometric sensor 100 to the neutral position once the force is removed. Moreover, the first bearing holder 130a and/or the second bearing holder 130b may include one or more surface features (e.g., ridges, protrusions, and/or the like) that interact with the first spring 126a and/or the second spring 126b to prevent the biometric sensor 100 from being shifted more than a threshold quantity beyond the neutral position. For example, the first bearing holder 130a and/or the second bearing holder 130b may include one or more surface features (e.g., ridges, protrusions, and/or the like) that interact with the first spring 126a and/or the second spring 126b to prevent the biometric sensor 100 from being tilted and/or rotated more than a threshold degrees from the neutral position. Alternatively and/or additionally, the first bearing holder 130a and/or the second bearing holder 130b may include one or more surface features (e.g., ridges, protrusions, and/or the like) that interact with the first spring 126*a* and/or the second spring 126*b* to prevent the biometric sensor 100 from being raised and/or lowered more than a threshold distance from the neutral position.

In some example embodiments, the biometric sensor 100 may include other features for imposing a positional limit on the self-adjusting mechanism. For example, the housing 132 may include one or more surface features (e.g., ridges, protrusions, and/or the like) that interacts with the first pivot hinge 124*a*, the first bearing holder 130*a*, the first spring 126*a*, the second pivot hinge 124*b*, the second bearing holder 130*b*, and/or the second spring 126*b* to prevent the biometric sensor 100 from being tilted, rotated, raised, and/or lowered more than a threshold quantity from the neutral position. One or more positional limits against the movement of the biometric sensor 100 may also be imposed by the first pivot hinge 124*a* and/or the second pivot hinge 124*b* having a limited range of motion.

Figure 8:
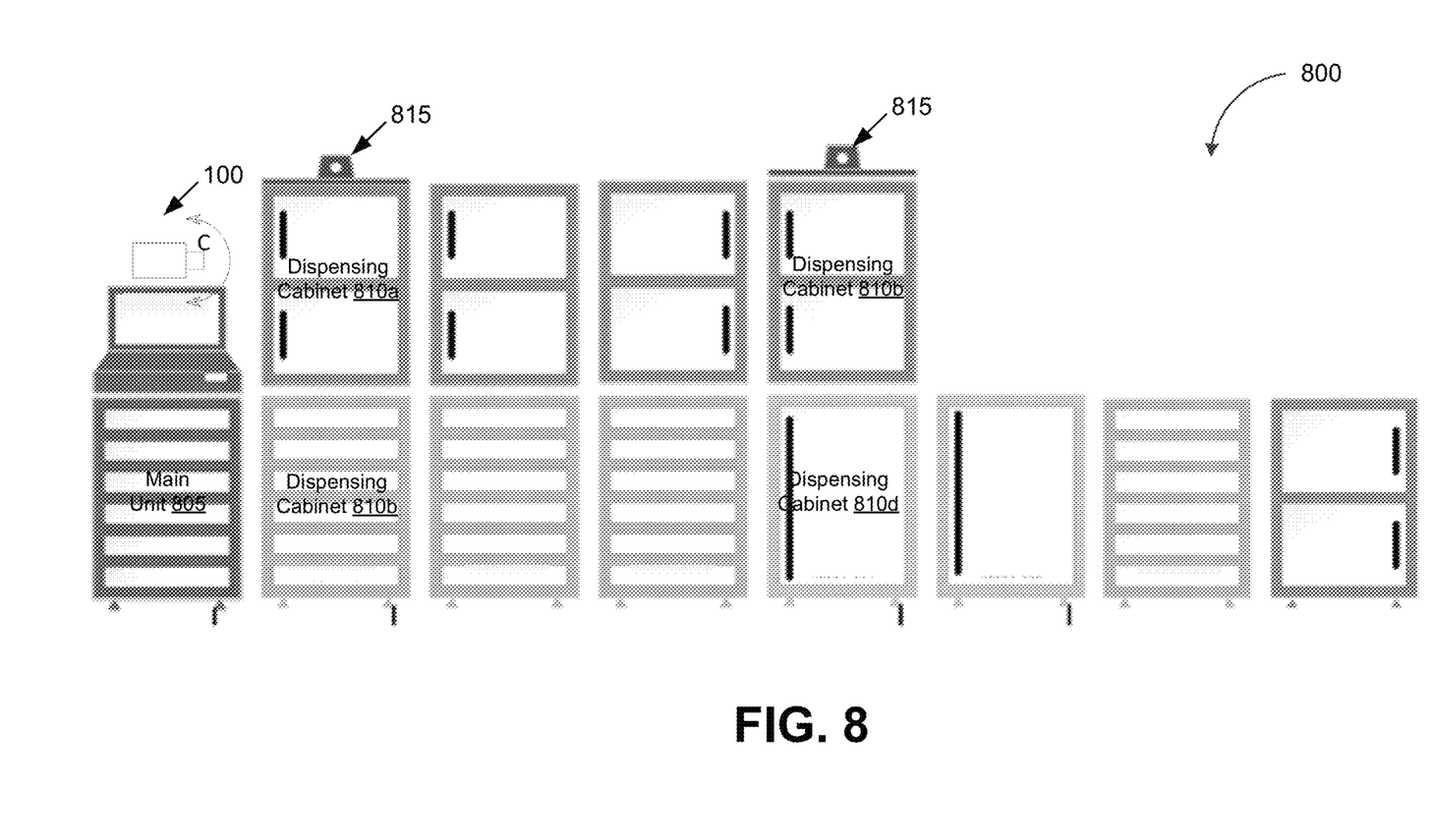
FIG. 8 depicts a schematic diagram illustrating an example of a medication management system, in accordance with some example embodiments.

FIG. 8 depicts a schematic diagram illustrating an example of a medication management system 800, in accordance with some example embodiments. The example of the medication management system 800 shown in FIG. 8 may include a main unit 805. The biometric sensor 100 may be mounted on the main unit 805 such that the users interacting with the medication management system 800 may be identified based at least on the biometric data captured by the biometric sensor 100. As noted, the neutral position of the biometric sensor 100 may be determined based at least on the mounting height and angle of the biometric sensor 100. Thus, in the example of the medication management system 800 shown in FIG. 8, the neutral position of the biometric sensor 100 may be configured to account for the height of the main unit 805. Moreover, as noted, the neutral position of the biometric sensor 100 may be determined based on the physical characteristic, such as a height distribution (e.g., mean, median, mode, range, and/or the like), of the users expected to interact with the biometric sensor 100 mounted on top of the first dispensing cabinet 810*a*. Accordingly, while in the neutral position, the field of view and/or the angle of view of the biometric sensor 100 may be suitable for capturing the biometric data of a threshold quantity of users interacting with the biometric sensor 100 mounted on top of the main unit 805.

Furthermore, the medication management system 800 shown in FIG. 8 may include one or more dispensing cabinet storing medications and supplies including, for example, a first dispensing cabinet 810*a* and a second dispensing cabinet 810*b*. Moreover, as shown in FIG. 8, the medication management system 800 may support a modular configuration in which the first dispensing cabinet 810*a* and the second dispensing cabinet 810*b* may be stacked on top of other dispensing cabinet such as a third dispensing cabinet 810*c* and a fourth dispensing cabinet 810*d*. One or more surveillance cameras 815 may be mounted on top of the first dispensing cabinet 810*a* and the second dispensing cabinet 810*b*. The one or more surveillance cameras 815 may be configured to capture images and/or videos of various activities at the medication management system 800 including, for example, one or more users interacting with the main unit 805, the first dispensing cabinet 810*a*, the second dispensing cabinet 810*b*, the third dispensing cabinet 810*c*, and the fourth dispensing cabinet 810*d*.

In some example embodiments, the biometric identifiers captured by the biometric sensor 100 at the main unit 805 may be used to control access to the main unit 805, the first dispensing cabinet 810*a*, the second dispensing cabinet 810*b*, the third dispensing cabinet 810*c*, and/or the fourth dispensing cabinet 810*d*. For example, upon receiving biometric data from an authorized user, a fastener (e.g., a latch, a lock, and/or the like) securing one or more of the main unit 805, the first dispensing cabinet 810*a*, the second dispensing cabinet 810*b*, the third dispensing cabinet 810*c*, and the fourth dispensing cabinet 810*d* may be released to provide access to the contents of therein. Moreover, the biometric identifiers captured by the biometric sensor 100 at the main unit 805 may be used to identify the users who appear in the footage captured by the one or more surveillance cameras 815.

Figure 9:
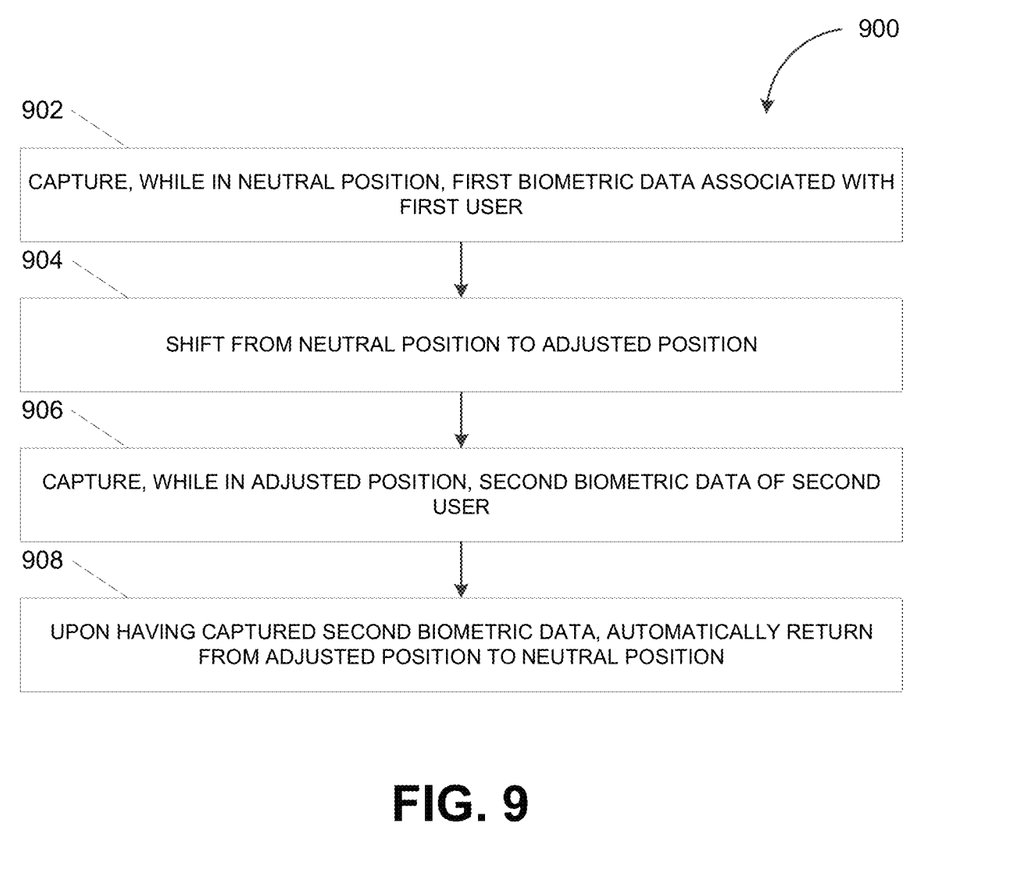
FIG. 9 depicts a flowchart illustrating an example of a process for biometric authentication, in accordance with some example embodiments.

FIG. 9 depicts a flowchart illustrating an example of a process 900 for biometric authentication, in accordance with some example embodiments. Referring to FIG. 9, the process 900 may be performed by the biometric sensor 100 to capture the biometric data of users with different physical characteristics. For example, the process 900 may be performed by the biometric sensor 100 in order to capture a first biometric data of a first user having a first height and a second biometric data of a second user having a second height. While the first user may be one of a majority of users whose eyes are in the field of view and/or angle of view of the biometric sensor 100 in the neutral position, the eyes of the second user may be outside of the field of view and/or angle of view of the biometric sensor 100 in the neutral position.

At 902, the biometric sensor 100 may capture, while in a neutral position, a first biometric data associated with a first user. In some example embodiments, the biometric sensor 100 in the neutral position may be configured to capture the biometric data of a threshold quantity of users interacting with the biometric sensor 100. For example, as noted, while the biometric sensor 100 is in the neutral position, the eyes of a majority of users may be within the field of view and/or angle of view of the biometric sensor 100. Because the biometric sensor 100 in the neutral position may be capable of capturing the biometric data associated with a majority of users, the biometric sensor 100 may be able to operate with minimal adjustments.

The neutral position of the biometric sensor 100 may be determined based at least on the physical characteristics of the users interacting with the biometric sensor 100 including, for example, a height distribution (e.g., mean, median, mode, range, and/or the like) of the users expected to interact with the biometric sensor 100. Moreover, the neutral position of the biometric sensor 100 may be determined based on the mounting height and/or mounting angle of the biometric sensor 100. For instance, in the example of the medication management system 800 shown in FIG. 8, the neutral position of the biometric sensor 100 may be determined based on the combined height of the first dispensing cabinet 810*a* and the third dispensing cabinet 810*c* atop which the biometric sensor 100 is mounted.

At 904, the biometric sensor 100 may shift from the neutral position to an adjusted position. In some example embodiments, the biometric sensor 100 may be configured to support various types of adjustments in order to capture the biometric data of users who are not within the field of view and/or angle of view of the biometric sensor 100 in the neutral position. For example, the position of the biometric sensor 100 may be adjusted by one or more rectilinear shifts along an x-axis, y-axis, and/or z-axis. Alternatively and/or additionally, the position of the biometric sensor 100 may be adjusted by rotating the biometric sensor 100 around a fixed axis. As shown in FIGS. 1-7, the self-adjusting mechanism included in the biometric sensor 100 may include one or more features configured to impose a limit on the magnitude (e.g., distance, angle, and/or the like) of the adjustment.

At 906, the biometric sensor 100 may capture, while in the adjusted position, a second biometric data associated with a second user. For example, while the biometric sensor 100 is in the adjusted position, the biometric sensor 100 may be able to capture the biometric data of users whose eyes are above or below the field of view and/or angle of view of the biometric sensor 100 in the neutral position.

At 908, the biometric sensor 100 may, upon having captured the second biometric data, automatically return from the adjusted position to the neutral position. In some example embodiments, the biometric sensor 100 may be configured to return to the neutral position. For example, as shown in FIGS. 1-7, the biometric sensor 100 may include an adjustment mechanism that includes, at one end of the biometric sensor 100, the first pivot hinge 124a coupled with the first spring 126a, the first bearing 128a, and the first bearing holder 130a. Furthermore, the adjustment mechanism may further include, at the opposite end of the biometric sensor, the second pivot hinge 124b that is coupled with the second spring 126b, the second bearing 128b, and the second bearing holder 130b. The first spring 126a and the second spring 126b may provide the force to return the biometric sensor 100 to the neutral position. Returning the biometric sensor 100 to the neutral position may ensure that the biometric sensor 100 may continue to operate with minimal adjustments.

In view of the above-described implementations of subject matter this application discloses the following list of examples, wherein one feature of an example in isolation or more than one feature of said example taken in combination and, optionally, in combination with one or more features of one or more further examples are further examples also falling within the disclosure of this application:

Item 1: A dispensing cabinet, comprising: a biometric sensor including a scanner configured to capture a biometric data, and an adjustment mechanism configured to respond to a force applied to the biometric sensor by shifting the biometric sensor from a neutral position to an adjusted position, the adjustment mechanism further being configured to respond to the removal of the force by returning the biometric sensor to the neutral position, the scanner being able to capture a first biometric data of a first user while the biometric sensor is in the neutral position, and the scanner being able to capture a second biometric data of a second user while the biometric sensor is in the adjusted position; a storage container; a fastener configured to secure one or more contents of the storage container; and a controller having at least one data processor configured to receive, from the biometric sensor, the first biometric data and/or the second biometric data, and control, based at least on the first biometric data and/or the second biometric data, the fastener securing the one or more contents of the storage container.

Item 2: The dispensing cabinet of Item 1, wherein the biometric sensor in the neutral position is able to capture the biometric data of a threshold quantity of users interacting with the dispensing cabinet including the first user.

Item 3: The dispensing cabinet of any one of Items 1 to 2, wherein the neutral position of the biometric sensor is determined based at least on a height and/or an angle at which the biometric sensor is mounted on the dispensing cabinet.

Item 4: The dispensing cabinet of any one of items 1 to 3, wherein the neutral position of the biometric sensor is determined based at least on one or more physical characteristics of users interacting with the dispensing cabinet.

Item 5: The dispensing cabinet of claim 4, wherein the one or more physical characteristics include a height distribution of the users interacting with the dispensing cabinet.

Item 6: The dispensing cabinet of any one of Items 1 to 5, wherein the neutral position of the biometric sensor is determined based at least on a frequency and/or a magnitude of adjustments made to the biometric sensor.

Item 7: The dispensing cabinet of any one of Items 1 to 6, wherein the adjustment mechanism includes a first assembly disposed on one end of the biometric sensor and a second assembly disposed on an opposite end of the biometric sensor, wherein the first assembly includes a first pivot hinge coupled with a first spring, a first bearing, and a first bearing holder, and wherein the second assembly includes a second pivot hinge coupled with a second spring, a second bearing, and a second bearing holder.

Item 8: The dispensing cabinet of Item 7, wherein the first spring and the second spring are configured to respond to the force by shifting the biometric sensor from the neutral position to the adjusted position, and wherein the first spring and the second spring are further configured to provide an opposite force for returning the biometric sensor to the neutral position.

Item 9: The dispensing cabinet of any one of Items 7 to 8, wherein the scanner is disposed on a printed circuit board assembly (PCBA) that is mechanically and electrically coupled to a cable, and wherein the cable is threaded through an aperture in the first assembly or the second assembly.

Item 10: The dispensing cabinet of Item 9, wherein the cable is configured to convey a signal between the scanner and the controller.

Item 11: The dispensing cabinet of any one of Items 9 to 10, wherein the biometric sensor further comprises a housing and a main body assembly configured to form a cavity when coupled with the housing, and wherein the printed circuit board assembly including the scanner is disposed at least partially inside the cavity.

Item 12: The dispensing cabinet of Item 11, wherein the biometric sensor further includes a front cover coupled with the main body assembly, and wherein the biometric sensor is configured to protect a lens assembly of the scanner included in the printed circuit board assembly.

Item 13: The dispensing cabinet of any one of Items 1 to 12, wherein the adjustment mechanism includes one or more features configured to prevent the biometric sensor from being shifted more than a threshold quantity beyond the neutral position.

Item 14: The dispensing cabinet of Item 13, wherein the one or more features include a ridge and/or a protrusion in a housing of the biometric sensor that interacts with a spring and/or a bearing holder to prevent the biometric sensor from being shifted more than the threshold quantity beyond the neutral position.

Item 15: The dispensing cabinet of any one of Items 13 to 14, wherein the one or more features include a ridge and/or a protrusion in a bearing holder that interacts with a spring to prevent the biometric sensor from being shifted more than the threshold quantity beyond the neutral position.

Item 16: The dispensing cabinet of any one of Items 13 to 15, wherein the one or more features include a hinge having a rotational limit.

Item 17: The dispensing cabinet of any one of Items 1 to 16, wherein the biometric data comprises palm veins, a facial geometry, a palm print, a hand geometry, an iris pattern, a retina pattern, a voice, a typing rhythm, a gait, and/or a signature.

Item 18: The dispensing cabinet of any one of Items 1 to 17, wherein the adjustment mechanism includes a motor, and wherein the controller is further configured to: determine a quality level of the first biometric data; determine the quality level is below a threshold quality level; and activate the motor to adjust the neutral position of the biometric scanner in order to increase the quality level of the second biometric data.

Item 19: The dispensing cabinet of any one of Items 1 to 18, wherein the controller is further configured to: detect the biometric sensor being shifted from the neutral position to the adjusted position; in response to detecting the biometric sensor being shifted from the neutral position to the adjusted position, record a magnitude of the shift and update a quantity of adjustments made to the biometric scanner; and in response to the quantity of adjustments exceeding a threshold value, provide an output indicating a recommended configuration for the biometric sensor, the recommended configuration corresponding to the magnitude of the shift recorded over a period of time.

Item 20: A method, comprising: capturing, by a scanner of a biometric sensor in a neutral position, a first biometric data of a first user, the biometric sensor having an adjustment mechanism configured to respond to a force applied to the biometric sensor by shifting the biometric sensor from the neutral position to an adjusted position, the adjustment mechanism further being configured to respond to the removal of the force by returning the biometric sensor to the neutral position, the scanner being able to capture the first biometric data of the first user while the biometric sensor is in the neutral position, and the scanner being able to capture a second biometric data of a second user while the biometric sensor is in the adjusted position; capturing, by the scanner of the biometric sensor in the adjusted position, the second biometric data of the second user; receiving, at a controller having at least one data processor, the first biometric data and/or the second biometric data from the biometric sensor; and controlling, by the controller and based at least on the first biometric data and/or the second biometric data, a fastener securing one or more contents of a storage container of a dispensing cabinet.

One or more aspects or features of the subject matter described herein, such as the controller associated with the biometric sensor 100, can be realized in digital electronic circuitry, integrated circuitry, specially designed ASICs, field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computing system may include clients and servers. A client and server are generally remote from each other and typically interact through a communication network. The relationship of client and server arises by virtue of computer programs running on the respective computers and having a client-server relationship to each other.

These computer programs, which can also be referred to as programs, software, software applications, applications, components, or code, include machine instructions for a programmable processor, and can be implemented in a high-level procedural and/or object-oriented programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example, as would a processor cache or other random access memory associated with one or more physical processor cores.

To provide for interaction with a user, one or more aspects or features of the subject matter described herein can be implemented on a computer having a display device, such as for example a cathode ray tube (CRT) or a liquid crystal display (LCD) or a light emitting diode (LED) monitor for displaying information to the user and a keyboard and a pointing device, such as for example a mouse or a trackball, by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including acoustic, speech, or tactile input. Other possible input devices include touch screens or other touch-sensitive devices such as single or multi-point resistive or capacitive track pads, voice recognition hardware and software, optical scanners, optical pointers, digital image capture devices and associated interpretation software, and the like.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." Use of the term "based on," above and in the claims is intended to mean, "based at least in part on," such that an unrecited feature or element is also permissible.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above. In addition, the logic flows depicted in the accompanying figures and/or described herein do not necessarily require the particular order shown, or sequential order, to achieve desirable results. Other implementations may be within the scope of the following claims.

What is claimed is:

1. A dispensing cabinet, comprising:
a biometric sensor including a scanner configured to capture a biometric data, and an adjustment mechanism configured to respond to a force applied to the biometric sensor by shifting the biometric sensor from a neutral position to an adjusted position, the adjustment mechanism further being configured to respond to the removal of the force by returning the biometric sensor to the neutral position, the scanner being able to capture a first biometric data of a first user while the biometric sensor is in the neutral position, and the scanner being able to capture a second biometric data of a second user while the biometric sensor is in the adjusted position, wherein the adjustment mechanism includes a first assembly disposed on one end of the biometric sensor and a second assembly disposed on an opposite end of the biometric sensor, wherein the first assembly includes a first pivot hinge coupled with a first spring, a first bearing, and a first bearing holder, and wherein the second assembly includes a second pivot hinge coupled with a second spring, a second bearing, and a second bearing holder;
a storage container;
a fastener configured to secure one or more contents of the storage container, the contents being related to medication; and
a controller having at least one data processor configured to receive, from the biometric sensor, the first biometric data and/or the second biometric data, and control, based at least on the first biometric data and/or the second biometric data, the fastener securing the one or more contents of the storage container.

2. The dispensing cabinet of claim 1, wherein the biometric sensor in the neutral position is able to capture the biometric data of a threshold quantity of users interacting with the dispensing cabinet including the first user.

3. The dispensing cabinet of claim 1, wherein the neutral position of the biometric sensor is determined based at least on a height and/or an angle at which the biometric sensor is mounted on the dispensing cabinet.

4. The dispensing cabinet of claim 1, wherein the neutral position of the biometric sensor is determined based at least on one or more physical characteristics of users interacting with the dispensing cabinet.

5. The dispensing cabinet of claim 4, wherein the one or more physical characteristics include a height distribution of the users interacting with the dispensing cabinet.

6. The dispensing cabinet of claim 1, wherein the neutral position of the biometric sensor is determined based at least on a frequency and/or a magnitude of adjustments made to the biometric sensor.

7. The dispensing cabinet of claim 1, wherein the first spring and the second spring are configured to respond to the force by shifting the biometric sensor from the neutral position to the adjusted position, and wherein the first spring and the second spring are further configured to provide an opposite force for returning the biometric sensor to the neutral position.

8. The dispensing cabinet of claim 1, wherein the scanner is disposed on a printed circuit board assembly (PCBA) that is mechanically and electrically coupled to a cable, and wherein the cable is threaded through an aperture in the first assembly or the second assembly.

9. The dispensing cabinet of claim 8, wherein the cable is configured to convey a signal between the scanner and the controller.

10. The dispensing cabinet of claim 8, wherein the biometric sensor further comprises a housing and a main body assembly configured to form a cavity when coupled with the housing, and wherein the printed circuit board assembly including the scanner is disposed at least partially inside the cavity.

11. The dispensing cabinet of claim 10, wherein the biometric sensor further includes a front cover coupled with the main body assembly, and wherein the biometric sensor is configured to protect a lens assembly of the scanner included in the printed circuit board assembly.

12. The dispensing cabinet of claim 1, wherein the adjustment mechanism includes one or more features configured to prevent the biometric sensor from being shifted more than a threshold quantity beyond the neutral position.

13. The dispensing cabinet of claim 12, wherein the one or more features include a ridge and/or a protrusion in a housing of the biometric sensor that interacts with a spring and/or a bearing holder to prevent the biometric sensor from being shifted more than the threshold quantity beyond the neutral position.

14. The dispensing cabinet of claim 12, wherein the one or more features include a ridge and/or a protrusion in a bearing holder that interacts with a spring to prevent the biometric sensor from being shifted more than the threshold quantity beyond the neutral position.

15. The dispensing cabinet of claim 12, wherein the one or more features include a hinge having a rotational limit.

16. The dispensing cabinet of claim 1, wherein the biometric data comprises palm veins, a facial geometry, a palm print, a hand geometry, an iris pattern, a retina pattern, a voice, a typing rhythm, a gait, and/or a signature.

17. The dispensing cabinet of claim 1, wherein the adjustment mechanism includes a motor, and wherein the controller is further configured to:
determine a quality level of the first biometric data;
determine the quality level is below a threshold quality level; and
activate the motor to adjust the neutral position of the biometric scanner in order to increase the quality level of the second biometric data.

18. The dispensing cabinet of claim 1, wherein the controller is further configured to:
detect the biometric sensor being shifted from the neutral position to the adjusted position;
in response to detecting the biometric sensor being shifted from the neutral position to the adjusted position, record a magnitude of the shift and update a quantity of adjustments made to the biometric scanner; and
in response to the quantity of adjustments exceeding a threshold value, provide an output indicating a recommended configuration for the biometric sensor, the recommended configuration corresponding to the magnitude of the shift recorded over a period of time.

19. A dispensing cabinet, comprising:
a biometric sensor including a scanner configured to capture a biometric data, and an adjustment mechanism configured to respond to a force applied to the biometric sensor by shifting the biometric sensor from a neutral position to an adjusted position, the adjustment mechanism further being configured to respond to the removal of the force by returning the biometric sensor to the neutral position, the scanner being able to capture a first biometric data of a first user while the biometric sensor is in the neutral position, and the scanner being able to capture a second biometric data of a second user while the biometric sensor is in the adjusted position, wherein the adjustment mechanism includes one or more features configured to prevent the biometric sensor from being shifted more than a threshold quantity beyond the neutral position, and wherein the one or more features include a hinge having a rotational limit;
a storage container;
a fastener configured to secure one or more contents of the storage container, the contents being related to medication; and
a controller having at least one data processor configured to receive, from the biometric sensor, the first biometric data and/or the second biometric data, and control, based at least on the first biometric data and/or the second biometric data, the fastener securing the one or more contents of the storage container.

20. A dispensing cabinet, comprising:
a biometric sensor including a scanner configured to capture a biometric data, and an adjustment mechanism configured to respond to a force applied to the biometric sensor by shifting the biometric sensor from a neutral position to an adjusted position, the adjustment mechanism further being configured to respond to the removal of the force by returning the biometric sensor to the neutral position, the scanner being able to capture a first biometric data of a first user while the biometric sensor is in the neutral position, and the scanner being able to capture a second biometric data of a second user while the biometric sensor is in the adjusted position, wherein the adjustment mechanism includes a motor:
a storage container;
a fastener configured to secure one or more contents of the storage container, the contents being related to medication; and
a controller having at least one data processor, the controller configured to:
receive, from the biometric sensor, the first biometric data and/or the second biometric data;
control, based at least on the first biometric data and/or the second biometric data, the fastener securing the one or more contents of the storage container
determine a quality level of the first biometric data;
determine the quality level is below a threshold quality level; and
activate the motor to adjust the neutral position of the biometric scanner in order to increase the quality level of the second biometric data.

21. A dispensing cabinet, comprising:
a biometric sensor including a scanner configured to capture a biometric data, and an adjustment mechanism configured to respond to a force applied to the biometric sensor by shifting the biometric sensor from a neutral position to an adjusted position, the adjustment mechanism further being configured to respond to the removal of the force by returning the biometric sensor to the neutral position, the scanner being able to capture a first biometric data of a first user while the biometric sensor is in the neutral position, and the scanner being able to capture a second biometric data of a second user while the biometric sensor is in the adjusted position;
a storage container;
a fastener configured to secure one or more contents of the storage container, the contents being related to medication; and
a controller having at least one data processor, the controller configured to:
receive, from the biometric sensor, the first biometric data and/or the second biometric data;
control, based at least on the first biometric data and/or the second biometric data, the fastener securing the one or more contents of the storage container;
detect the biometric sensor being shifted from the neutral position to the adjusted position;
in response to detecting the biometric sensor being shifted from the neutral position to the adjusted position, record a magnitude of the shift and update a quantity of adjustments made to the biometric scanner; and
in response to the quantity of adjustments exceeding a threshold value, provide an output indicating a recommended configuration for the biometric sensor, the recommended configuration corresponding to the magnitude of the shift recorded over a period of time.

* * * * *